US009149195B2

(12) United States Patent
Hadley

(10) Patent No.: US 9,149,195 B2
(45) Date of Patent: Oct. 6, 2015

(54) METHODS AND APPARATUS FOR QUANTIFYING THE RISK OF CARDIAC DEATH USING EXERCISE INDUCED HEART RATE RECOVERY METRICS

(75) Inventor: David M. Hadley, Woodinville, WA (US)

(73) Assignee: Mortara Instrument, Inc., Milwaukee, WI (US)

( * ) Notice: Subject to any disclaimer, the term of this patent is extended or adjusted under 35 U.S.C. 154(b) by 1456 days.

(21) Appl. No.: 11/733,699

(22) Filed: Apr. 10, 2007

(65) Prior Publication Data

US 2007/0249949 A1   Oct. 25, 2007

Related U.S. Application Data

(60) Provisional application No. 60/793,744, filed on Apr. 21, 2006.

(51) Int. Cl.
| | |
|---|---|
| *A61B 5/04* | (2006.01) |
| *A61B 5/024* | (2006.01) |
| *A61B 5/0452* | (2006.01) |
| *A61B 5/00* | (2006.01) |
| *G06F 19/00* | (2011.01) |
| *A61B 5/22* | (2006.01) |

(52) U.S. Cl.
CPC ............. *A61B 5/024* (2013.01); *A61B 5/0452* (2013.01); *A61B 5/4035* (2013.01); *A61B 5/4884* (2013.01); *A61B 5/7275* (2013.01); *G06F 19/3431* (2013.01); *G06F 19/3437* (2013.01); *G06F 19/3487* (2013.01); *A61B 5/222* (2013.01)

(58) Field of Classification Search
USPC .......... 600/508, 509, 513, 519–521
See application file for complete search history.

(56) References Cited

U.S. PATENT DOCUMENTS

| | | | |
|---|---|---|---|
| 5,148,812 A | 9/1992 | Verrier et al. | |
| 5,437,285 A | 8/1995 | Verrier et al. | |
| 5,682,900 A | 11/1997 | Arand et al. | |
| 5,713,367 A | 2/1998 | Arnold et al. | |
| 5,755,671 A | 5/1998 | Albrecht et al. | |
| 6,648,829 B2 | 11/2003 | Starobin et al. | |
| 7,031,766 B1 * | 4/2006 | Paris ............................ | 600/519 |
| 7,136,694 B2 | 11/2006 | Hadley et al. | |
| 7,151,957 B2 | 12/2006 | Beker et al. | |
| 7,167,744 B2 | 1/2007 | Hadley et al. | |

(Continued)

OTHER PUBLICATIONS

Takashi, Y. et al. Characteristics of Heart Rate Decay Regulated by Neural Component after Dynamic Exercise in Athletes. (1999) Respiration and Circulation. vol. 47, No. 6. pp. 627-633.*

(Continued)

*Primary Examiner* — Erica Lee
(74) *Attorney, Agent, or Firm* — Reinhart Boerner Van Deuren s.c.

(57) ABSTRACT

Methods and apparatus for assessing cardiac risks based on heart activity data obtained during a recovery stage of an exercise test of a specific patient. An embodiment of a method comprises determining a prognostic period of the heart activity data after a time $t_0$ after a peak heart rate of the exercise test, and ascertaining a risk indicator. The risk indicator is based on (a) the heart rate activity data during the recovery stage only after time $t_0$ and (b) a post-exercise heart rate reserve based on a post-exercise resting heart rate. This embodiment of the method further includes providing an assessment of cardiac risk of a specific patient based on the ascertained risk indicator.

20 Claims, 8 Drawing Sheets

(56) References Cited

U.S. PATENT DOCUMENTS

| | | | |
|---|---|---|---|
| 7,167,745 | B2 | 1/2007 | Hadley et al. |
| 7,174,204 | B2 | 2/2007 | Hadley et al. |
| 7,277,756 | B2* | 10/2007 | Smith et al. ............... 607/18 |
| 2003/0013979 | A1* | 1/2003 | Dardik et al. ............. 600/520 |
| 2003/0149370 | A1 | 8/2003 | Starobin et al. |
| 2005/0038351 | A1 | 2/2005 | Starobin et al. |
| 2005/0065443 | A1* | 3/2005 | Ternes ..................... 600/509 |
| 2007/0208266 | A1 | 9/2007 | Hadley |

OTHER PUBLICATIONS

Lipinski, M.J. et al. Novel Heart Rate Recovery Constant Predicts the Presence and Severity of Coronary Artery Disease. (2003) Journal of the American College of Cardiology. vol. 41, No. 6. pp. 166 and Lauer, M.S. et al. Timing of Heart Rate Decay After Exercise and Mortality. (2003) Journal of the American College of Cardiology. vol. 41, No. 6.*

International Search Report and Written Opinion for PCT/US2007/066349, mailed Dec. 26, 2007.

U.S. Appl. No. 11/681,099, filed Mar. 1, 2007, Hadley.

Arai Y, Saul JP, Albrecht P, Hartley LH, Lilly LS, Cohen RF, and Colucci W., *Modulation of Cardiac Autonomic Activity During and Immediately After Exercise*, Am.J.Physiol. 1989, H132-H141.

Van Ravenswaaij CMA, Kollee LAA, Hopman JCW, Stoelinga GBA, and van Geijn HP, *Heart Rate Variability*, Annals of Internal Medicine 1993, 118(6): 435-447.

Nolan J, et al., *Prospective Study of Heart Rate Variability and Mortality in Chronic Heart Failure*, Circulation 1998, 98:1510-1516.

Eckberg DL, *Sympathovagal Balance—A Critical Appraisal*, Circulation 1997; 96:3224-3232.

Kannankeril PJ, and Goldberger JJ, *Parasympathetic Effects on Cardiac Electrophysiology During Exercise and Recovery*, AM J Physiol Heart Circ. Physiol 2002; 282:H2091-H2098.

Tsuji H, Larson MG, Venditti FG, Manders ES, Evans JC, Feldman CL, and Levy D, *Impact of Reduced Heart Rate Variability on Risk for Cardiac Events—The Framingham Heart Study*, Circulation 1996, 94:2850-2855.

Chiou CW, and Zipes DP, *Selective Vagal Denervation of the Atria Eliminates Heart Rate Variability and Baroreflex Sensitivity While Preserving Ventricular Innervation*, Circulation 1998; 98:360-368.

Goldberger JJ, Challapalli S, Tung R, Parker MA, and Kadish AH, *Relationship of Heart Rate Variability to Parasympathetic Effect*, Circulation 2001, 103:1977-1983.

Goldberger JJ, Ahmed MW, Parker MA, and Kadish AH, *Dissociation of Heart Rate Variability from Parasympathetic Tone*, Am. J. Physiol. 1994; 266:H2152-H2157.

Pichon AP, de Bisschop C, Roulaud M, Denjean A, and Papelier Y, *Spectral Analysis of Heart Rate Variability During Exercise in Trained Subjects*, Med. Sci. Sports Exerc. 2004, 36(10):1702-1708.

Zipes DP and Wellens HJJ. *Sudden Cardiac Death*. Circulation. 1998;98:2334-2351.

Schwartz PG, LA Rovere MT an Vanoli E. *Autonomic Nervous System and Sudden Cardiac Death*. Circulation. 1992; 85(suppl 1):1-77-1-91.

Imai K, Sato H., Hori M, Kusuoka H, Ozki H, Yokoyama H, Takeda H, Inoue M, and Kamada T. *Vagally Mediated Heart Rate Recovery After Exercise is Accelerated in Athletes but Blunted in Patients With Chronic Heart Failure*. JACC. 1994; 24(6):1529-35.

Kannankeril PJ, LE FK, Kadish AH and Goldberger JJ. *Parasympathetic Effects on Heart Rate Recovery After Exercise*. J Investigative Med. 2004;52(6):394-401.

Nishime EO, Cole CR, Blackstone EH, Pashkow FJ, and Luer MA. *Heart Rate Recovery and Treadmill Exercise Score as Predictors of Mortality in Patients Referred for Exercise ECG*. JAMA. 2000; 284(11):1392-8.

Cole CR, Foody JM, Blackstone EH and Lauer MS. *Heart rate recovery after Submaximal Exercise Testing as a predictor of Mortality in Cardiovascularly Healthy Cohort*. Ann Intern Med. 2000;132:552-555.

Shelter K, Marcus R, Froelicher VF, Vora S, Kalisetti D, Prakash M, DO D, and Myers J. *Heart Rate Recovery: Validation and Methodologic Issues*. JACC. 2001; 38(7):1980-7.

Nissinen SI, Makikallio TT, Seppanen T, Tapanainen JM, Salo M, Tulppo MP and Huikuri HV. *Heart Rate Recovery After Exercise as a Predictor of Mortality Among Survivors of Acute Myocardial Infarction*. AM J. Cardiol. 2003; 91:711-4.

Mark DB, Shaw L, Harrell FE, Hlatky MA, Lee KL, Bengtson Jr, McCants CB, Calif RM and Pryor DB. *Prognostic Value of a Treadmill Exercise Score in Outpatients With Suspected Coronary Artery Disease*. N Eng. J Med. 1991;325(12):849-53.

International Search Report and Written Opinion for International App. No. PCT/US07/63096, mailed Mar. 3, 2008.

Cole CR, Blackstone EH, Pashkow FJ, Snader CE and Lauer MS. *Heart-Rate Recovery Immediately After Exercise as a Predictor of Mortality*. N Eng J Med. 1999;341:1351-7.

Morshedi-Meibodi A, Larson MG, Levy D, O'Donnell CJ, Vasan RS. *Heart Rate Recovery After Treadmill Exercise Testing and Risk of Cardiovascular Disease Events (The Framingham Heart Study)*. Am J. Cardiol. 2002; 90:848-52.

Vivekananthan DP, Blackstone EH, Pothier CE, and Lauer MS. *Heart Rate Recovery After Exercise Is a Predictor of Mortality, Independent of the Angiographic Severity of Coronary Disease*. J. Am. College Cardiology. 2003; 42(5):831-8.

Mora S, Redberg RF, Cui Y, Whiteman MK, Flaws JA, Sharrett AR, and Blumenthal RS. *Ability of Exercise Testing to Predict Cardiovascular and All-Cause Death in Asymptomatic Women*. JAMA. 2003; 290(12)1600-7.

Racine NR, Blanchet M, Ducharme A, Marquis J, Boucher JM, Juneau M and White M. *Decreased Heart Rate Recovery After Exercise in Patients With Congestive Heart Failure: Effect of Beta-Blocker Therapy*. J. Cardiac Failure. 2003; 9(4):296-302.

Gibbons R. *Commentary: Abnormal Heart-Rate Recovery After Exercise*. The Lancet. 2002; 359:1536-7.

Desai M, De la Pena-Almaguer E. and Mannting F. *Abnormal Heart Rate Recovery After Exercise as a Reflection of an Abnormal Chronotropic Response*. Am J. Cardiol. 2001; 87:1164-1169.

Franklin, JN. *Well-posed stochastic extension of ill-posed linear problems*. J. Math. Anal. Appl. 1970; 31:682-716.

Wiggins, RA. *The general linear inverse problem: Implications of surface waves and free oscillations for earth structure*. Rev. Geophys and Space Phys. 1972; 10:251-285.

File History for U.S. Appl. No. 11/681,099, filed Sep. 6, 2007.

Cook NR., "Use and misuse of the receiver operating characteristic curve in risk prediction", *Circulation*, 2007;115:928-35.

Jouven X, Empana J-P, Schwartz PJ, Desnos M, Courbon D, Ducimetiere P., "Heart-Rate profile during exercise as a predictor of sudden death", *n Engl J Med.*, 2005;352:1951.

Lauer MS, Okin PM, Larson MG, Evans JC, D Levy, "Impaired heart rate response to graded exercise: prognostic implications of chronotropic incompetence in the Framingham Heart Study", *Circulation*, 1996;93:1520.

Myers J, Bader D, Madhavfen R, Froelicher V., "Validation of a specific activity questionnaire to estimate exercise tolerance in patients referred for exercise testing", *Am Heart J.*, 2001;142:1041.

Bigger et al., *Frequency Domain Measures of Heart Period Variability and Mortality After Myocardial Infarction*, Circulation, vol. 85, No. 1, Jan. 1, 1992, pp. 164-171.

Stein Phyllis et al., *Non-Linear Heart Rate Variability and Risk Stratification in Cardiovascular Disease*, Indian Pacing and Electrophysiology Journal, vol. 5, No. 3, 2005, pp. 210-220.

Mateo et al., *ECG-Based Clinical Indexes During Exercise Test Including Repolarization, Depolarization and HRV*, Computer in Cardiology, vol. 28, Sep. 23, 2001, pp. 309-312.

Freeman et al., *Autonomic Nervous System Interaction with the Cardiovascular System During Exercise*, Progress in Cardiovascular Diseases, vol. 48, No. 5, Mar. 1, 2006, pp. 342-362.

European Application No. EP07757740, Supplementary European Search Report, Apr. 30, 2010, 10 pages.

* cited by examiner $$HR = HR_{rec} + (HR_{peak} - HR_{rec}) \cdot e^{-k(t-t_0)}$$

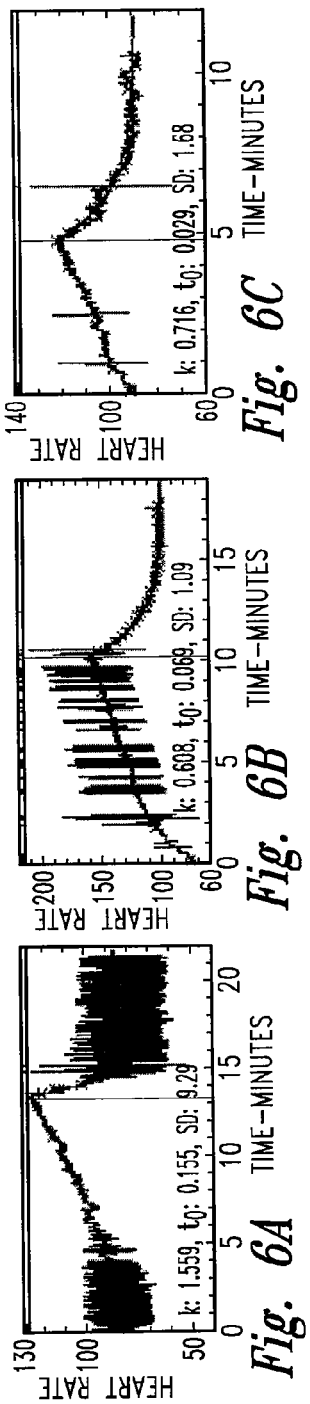
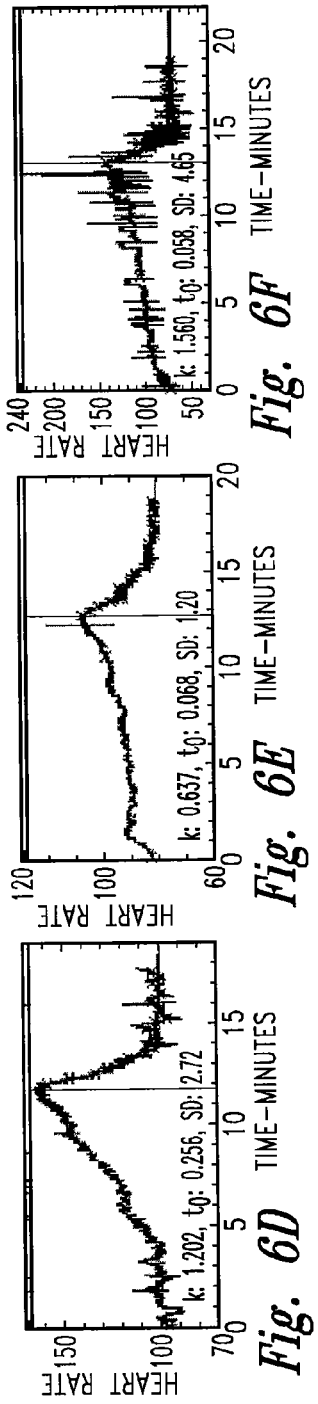
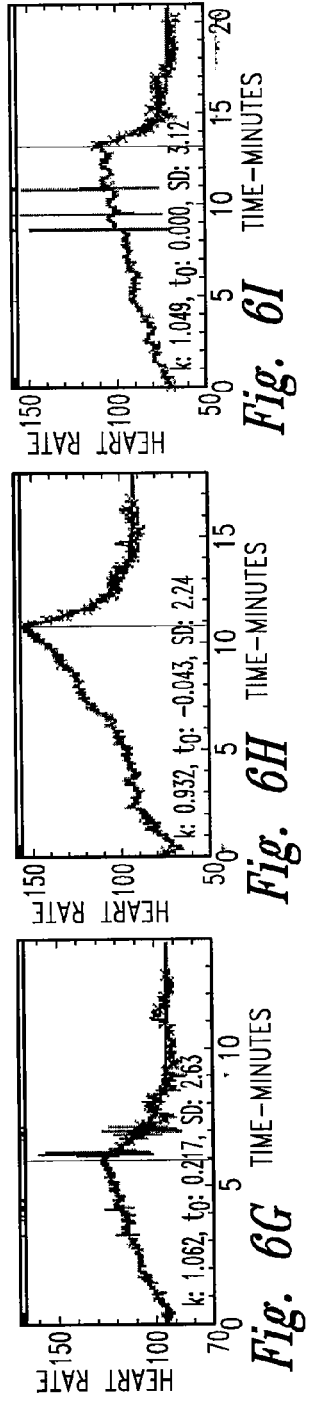
Fig. 6A  Fig. 6B  Fig. 6C
Fig. 6D  Fig. 6E  Fig. 6F
Fig. 6G  Fig. 6H  Fig. 6I

METHODS AND APPARATUS FOR QUANTIFYING THE RISK OF CARDIAC DEATH USING EXERCISE INDUCED HEART RATE RECOVERY METRICS

CROSS-REFERENCE TO RELATED APPLICATION

This application claims the benefit of U.S. Provisional Patent Application No. 60/793,744, filed Apr. 21, 2006, which is incorporated herein by reference in its entirety.

TECHNICAL FIELD

The present invention relates to methods and apparatus for using heart rate measurements made during cardiac stress testing to determine the normalized slope of the heart rate recovery curve and a prognostic period to measure the normalized slope for assessing the risk of death of a patient.

BACKGROUND

Sudden cardiac death (SCD) accounts for 300,000-400,000 deaths per year in the United States. Although the individual risk of SCD in the adult U.S. population is only about 0.1-0.2% per year, when applied to the large population base of the U.S., SCD is often the first and only manifestation of cardiovascular disease in a majority of cardiovascular related deaths. Deaths from patients recovering from large myocardial infarctions actually represent the minority of the total deaths per year. As a result, a low cost screening tool that would provide early detection of patients at risk for SCD would be tremendously valuable for early treatment and intervention.

However, it can be difficult to accurately predict or assess the risk of SCD because many underlying pathologies support or trigger the events leading to SCD instead of any single condition. Of these various conditions, most data suggests that autonomic regulation of the heart through the branches of the sympathetic and vagal systems is extremely important in maintaining stable rhythms. In particular, it appears that vagal stimulation mitigates the development of ventricular arrhythmias in a variety of experimental studies. A strong vagal response appears to lower heart rate and lower the risk of arrhythmia, which effectively counteracts reflex sympathetic hyperactivity and provides a key determinant for survival.

The dual branches of the autonomic system regulate heart rate over the course of an exercise test. Increasing exertion during exercise increases perfusion demands and results in a higher heart rate. The higher heart rate is caused by increased activity of the sympathetic system and decreased parasympathetic regulation. During an initial stage of recovery after terminating exercise, sympathetic stimulation is withdrawn. After the initial stage of recovery, vagal mediation necessary to return the heart rate to a resting value is reasserted to further reduce the heart rate. Heart rate recovery parameters, measured as the difference between the peak heart rate and the heart rate at subsequent times during recovery (e.g., 1 or 2 minutes into recovery), provide a gross quantification of the combined effects on heart rate from the activities of both sympathetic and vagal branches of the autonomic system. Numerous studies have examined the prognostic value of heart rate recovery parameters for assessing patient risk based on the vagal contribution to the recovery and the relationship between poor vagal tone and cardiovascular-related mortality. Even when key co-morbidities were quantified, such as perfusion defects and coronary artery disease (CAD), the heart rate recovery has been found to be a significant and independent predictor of all-cause death.

Reassertion of vagal tone (i.e., vagal mediation) following exercise is an important component in the heart rate recovery process. It has been found that patients with poor vagal tone are at increased risk of cardiovascular mortality, and many heart rate recovery studies have attempted to accurately quantify the vagal tone during recovery. However, it is not clear that traditional measures of evaluating the heart rate recovery accurately quantify the vagal tone. More specifically, traditional measures of evaluating the heart rate recovery of a specific patient may be adversely influenced by the sympathetic withdrawl. Heart rate recovery is also strongly correlated with, and becomes identical to, the heart rate reserve as recovery time increases. The heart rate reserve in such traditional studies is the peak heart rate less a measured pre-exercise supine resting heart rate. Additionally, normalizing a heart rate recovery value of traditional techniques by the heart rate reserve and assessing the result as a percentage of total recovery renders the index non-prognostic. This raises further concerns that traditional techniques for evaluating the heart rate recovery of a patient may have questionable value in characterizing vagal tone.

Although the traditional methods for measuring heart rate recovery are well known to practitioners of the art, and important observations have been made in many previous studies, the works of Cardiac Science, Inc. and others suggest that such traditional methods for evaluating heart rate recovery result in a disguised metric for peak heart rate or heart rate reserve. As a result, traditional methods for evaluating heart rate recovery fail to accurately quantify the vagal tone of a specific patient. Therefore, it would be beneficial to extract vagal tone information in a way that is both prognostic and independent of peak heart rate and traditional heart rate reserve parameters to provide a new and accurate parameter for patient risk stratification.

BRIEF DESCRIPTION OF THE DRAWINGS

FIGS. 6A-6I illustrate a representative suite of patient exercise tests and the exponential curves fit to the data for each recovery period.

DETAILED DESCRIPTION

Figure 1:
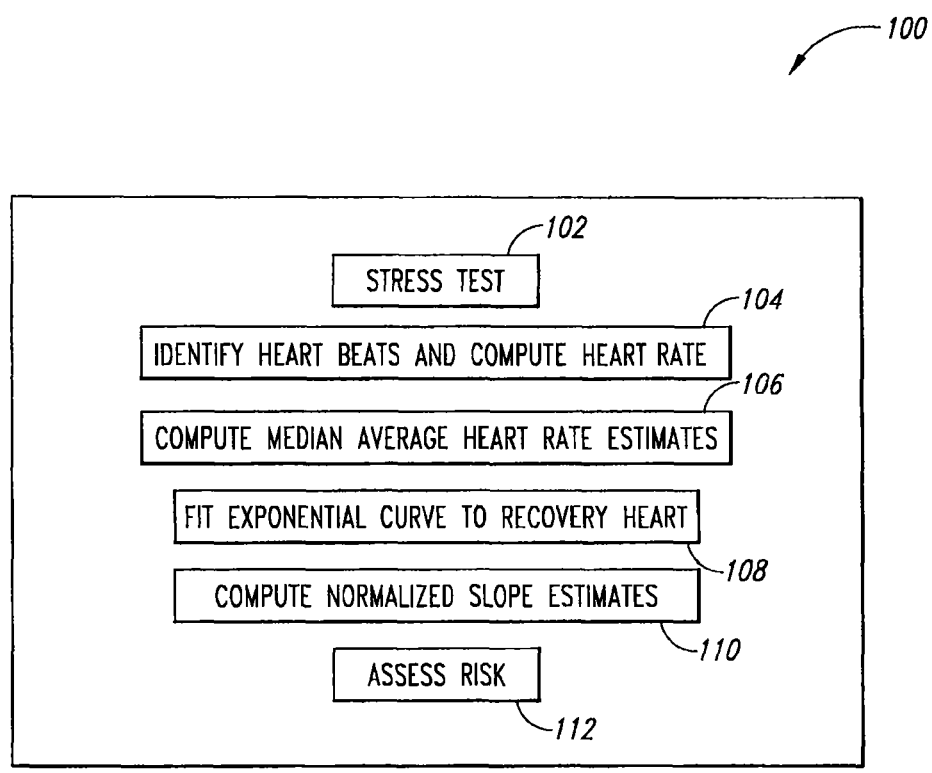
FIG. 1 is a flow chart illustrating a method for determining the risk of cardiovascular death from analysis of heart rate recovery data in accordance with an embodiment of the invention.

Several specific embodiments of methods and apparatus are described below in a manner sufficient to enable a person skilled in the art to practice the invention. The invention, however, can include additional embodiments that may not have all of the features described below or that may have additional or different features. Thus, the present invention is not intended to be limited to the embodiments presented, but is to be accorded the widest scope consistent with the claims.

A. Overview

The present invention is directed toward methods and apparatus for accurately quantifying the risk of a cardiac event using exercise induced heart rate recovery metrics. One aspect of the invention is a method for assessing cardiac risks based on heart activity data obtained during a recovery stage of an exercise test of a specific patient. An embodiment of such a method comprises determining a prognostic period of the heart activity data after a time $t_0$ after a peak heart rate of the exercise test, and ascertaining a risk indicator. The risk indicator is based on (a) the heart rate activity data during the recovery stage only after time $t_0$ and (b) a post-exercise heart rate reserve based on a post-exercise resting heart rate. This embodiment of the method further includes providing an assessment of cardiac risk of a specific patient based on the ascertained risk indicator.

Another embodiment of a method for assessing cardiac risks further includes determining the time $t_0$ and the post-exercise resting heart rate by (a) measuring the peak heart rate at a time t at which the patient terminates exercising and (b) fitting the time $t_0$ in the post-exercise resting heart rate to the heart activity data during the recovery stage. This embodiment of the method further comprises determining a compensated curve of the heart rate activity defined by a heart rate during the prognostic period and the post-exercise resting heart rate. One example of this embodiment defines a post-exercise heart rate reserve as the difference between the peak heart rate and the post-exercise resting heart rate (the recovery heart rate).

Another embodiment of a method for assessing cardiac risks based on heart activity data comprises determining a post-exercise resting heart rate and a prognostic period after a time $t_0$ after a peak heart rate in which $t_0$ defines an effective start of the recovery. This method further includes determining a slope of a post-exercise heart rate recovery after time $t_0$ based on the post-exercise resting heart rate, and providing a cardiac risk assessment of the patient based on the determined slope of the heart rate recovery curve.

Another embodiment of a method for assessing cardiac risks in accordance with the invention comprises providing heart rate recovery slopes of a cohort with a population that has experienced a cardiac event and providing heart rate recovery slopes of a cohort of the population that has not experienced a cardiac event. The embodiment of this method further includes selecting a prognostic period of the recovery stage for the specific patient where the heart rate recovery slope of the population that has not experienced a cardiac event is statistically separate from the heart rate recovery slope of the cohort of the population that has experienced a cardiac event. The method further includes determining a heart rate recovery slope of the patient during the prognostic period, and ascertaining the cardiac risk for the patient based on the heart rate recovery slope of the patient, the heart rate recovery slope of the cohort that has experienced a cardiac event, and the heart rate recovery slope of the cohort that has not experienced a cardiac event.

Still another embodiment of a method for assessing cardiac risks in accordance with the invention comprises providing a prognostic period during the recovery stage after sympathetic control of the heart is subordinate to vagal control of the heart. This method further includes ascertaining a cardiac risk for the patient based on a slope of the heart activity data during only the prognostic period.

Another aspect of the invention is a system for assessing cardiac risks based on heart activity data obtained during a recovery stage of an exercise test of a specific patient. An embodiment of such a system comprises a cardiographic device configured to measure the heart activity data and a computer having a computer-operable medium. The computer-operable medium contains instructions that determines a prognostic period of the heart activity data after a time $t_0$ after a peak heart rate of the exercise test, and ascertains a risk indicator. The risk indicator is based on (a) the heart rate activity data obtained during the recovery stage only after time $t_0$ and (b) a post-exercise heart rate reserve value based on a post-exercise resting heart rate. The instructions of the computer-operable medium also provide an assessment of cardiac risk of a specific patient based on the ascertained risk indicator.

Another embodiment of a system for assessing cardiac risks includes a cardiographic device configured to measure the heart activity data and a computer having a computer-operable medium containing instructions that determines a post-exercise resting heart rate and a start of a prognostic period after a time $t_0$ after a peak heart rate, wherein the time $t_0$ defines an effective start to recovery. The instructions of the computer-operable medium also determines a slope of a post-exercise heart rate recovery after time $t_0$ based on the post-exercise resting heart rate, and provides a cardiac risk assessment of the patient based on the determined slope of the heart rate recovery.

FIG. 1 is a flow chart of a method 100 for quantifying the risk of cardiovascular death using an exercise induced normalized heart rate recovery slope metric as a risk indicator. The method 100 includes a first stage 102 comprising increasing the patient's heart rate and recording the electrocardiographic (ECG) signals representative of the electrical signal of the beating heart. The recorded ECG signals provide heart rate activity data from which the normalized heart rate recovery slope metric can be obtained. This may be accomplished through standard cardiac stress exercise protocols well known to practitioners of the art. Method 100 continues to a second stage 104 that analyzes the digitized ECG signal to identify each heart beat and compute the heart rate. In several embodiments, the heart rate information is next partitioned into consecutive time windows extending from the end of exercise through the end of recovery and the statistical measures of median average and standard deviation are computed for each time window at a third stage 106. The method can further include a fourth stage 108 in which the median average estimates, weighted by the associated standard deviations, are fit with an exponential curve. The post-exercise heart rate reserve and the start of recovery information developed in the fourth stage 108 are used in a fifth stage 110 to compute various normalized estimates of a heart rate recovery slope (HRRS) metric over relevant time windows. The normalized HRRS metrics are used in a sixth stage 112 to assess the patient's risk of cardiovascular death.

B. Stimulating the Heart and Computing Heart Rate—Stages 102 & 104

The first stage 102 of the method 100 includes stimulating the heart to beat at a faster rate and recording the resulting electrical signals. The heart rate can be elevated to maximum capacity via exercise on a treadmill, ergometer, or other exercise device. In cardiac stress tests, a plurality of electrodes (e.g., ten) are generally placed across the shoulders and chest to obtain spatial resolution of distinct aspects of the ECG waveform. However, for analysis of the heart rate recovery, it is only necessary to determine the time of each beat. This can be accomplished with a single trace measuring the ECG voltage across two points on the chest. In many embodiments of the method 100, time resolution is valuable and the ECG voltage(s) should be digitized at a diagnostic resolution of 500 or more samples per second. Most commonly, the stage 102 will be carried out in the clinical environment of a cardiac stress test as is well known in the field of cardiac stress testing.

Figure 2:
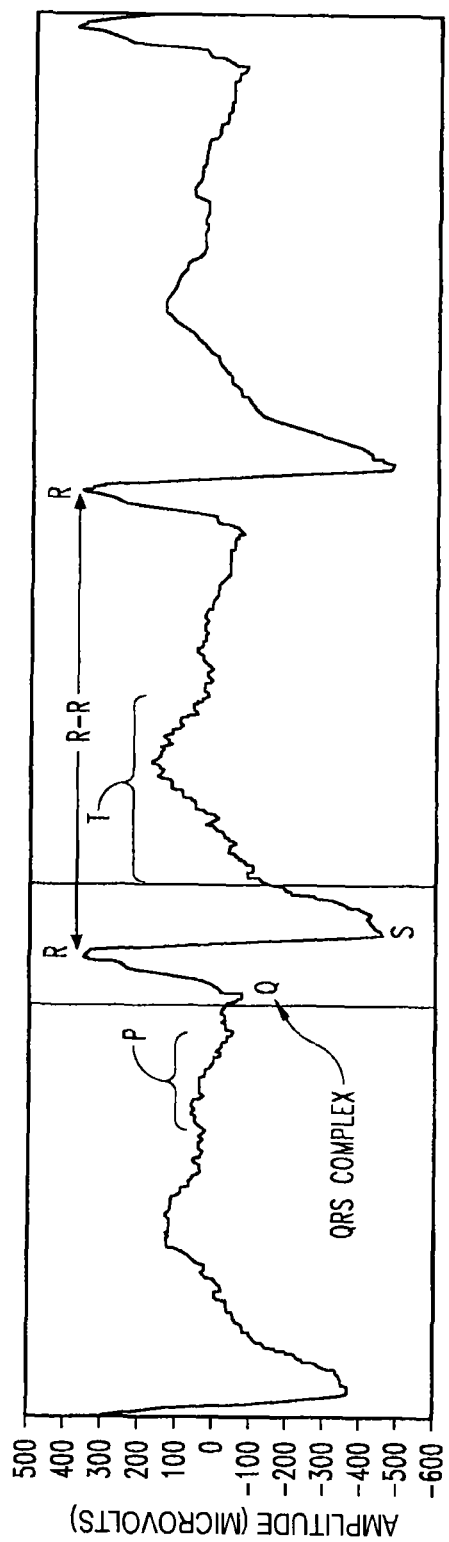
FIG. 2 is a graph illustrating an ECG and the reference points corresponding to activation and recovery of the Atria (P); the ventricle activation phases Q, R and S, forming the QRS complex; the recovery or re-polarization phase T of the ventricles; and the R-R time interval between consecutive beats as measured between the peaks of the R phase.

FIG. 2 illustrates an example of an ECG trace of a small number of heart beats in which the key phases of a heart beat are identified. The normal heart beat starts in the upper chambers of the heart (atria) and the initial ECG phase that records this activation is termed the P-wave; the bracket indicates the duration of the P-wave portion of the heart beat. Following the activation of the atria, the blood moves into the lower chambers of the heart (ventricles) and activation of the ventricle muscle both pumps the blood to the body and generates the ECG phases Q, R and S (often referred to as the QRS complex). The ventricle muscles recover (repolarize) in anticipation of the next beat, creating the T-wave signal on the ECG. The time interval between adjacent beats is generally measured between the peaks of the R wave and is referred to as the R-R interval. A more robust measure of R-R intervals, particularly when the peak of the R wave is not sharp, can be obtained by cross-correlating the QRS complex from an average or median beat with each subsequent beat and noting the time of maximum correlation.

Figure 3:
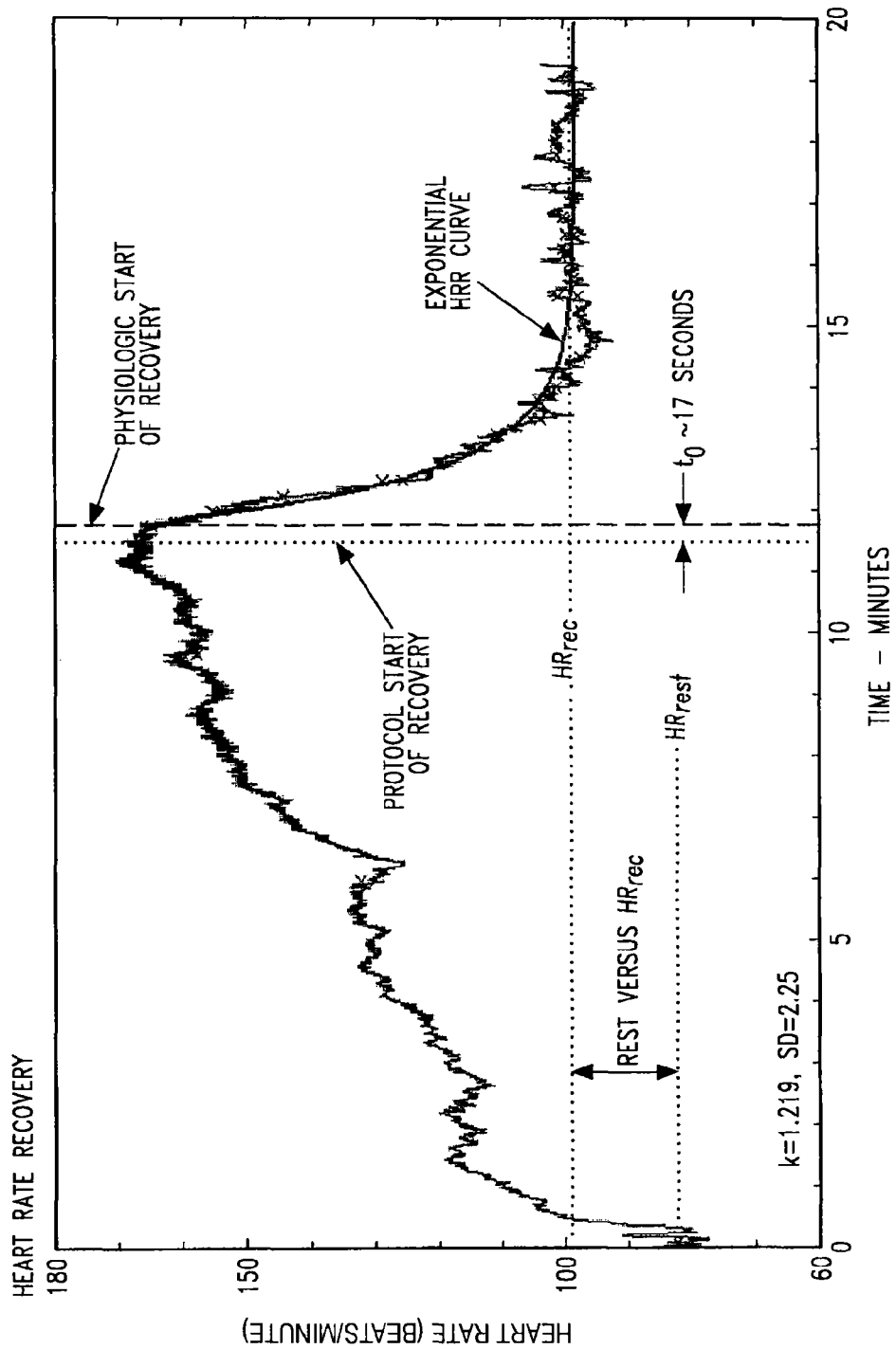
FIG. 3 is a graph showing heart rate activity data over the course of an exercise stress test and the exponential decay of heart rate during recovery.

For every beat detected the instantaneous heart rate; measured in beats per minute, for heart rate recovery analysis is computed from the R-R interval between the current and preceeding beats by the simple equation HR=60/(R-R), where the R-R interval is measured in seconds. FIG. 3 shows a typical plot of continuous heart rate during a stress test. Note the heart rate starts at time 0 at about 90 beats/minute, climbs to a peak of over 160 beats/minute at peak exercise, and then declines rapidly as the patient recovers.

C. Computing the Normalized Slope—Stages 106 through 110

The method 100 includes determining a prognostic period of the heart activity data after a time $t_0$ after a peak heart rate of the exercise test, and ascertaining a risk indicator based on the heart activity data during the recovery stage only after the time $t_0$ and a post-exercise heart rate reserve based on a post-exercise resting heart rate. In several embodiments, the risk indicator is the normalized slope of a heart rate recovery curve during the prognostic period. As such, several embodiments of the method 100 are directed toward computing the normalized slope of the heart rate recovery curve during a specific prognostic period. As explained in more detail below, the time $t_0$ and the post-exercise resting heart rate are used to determine a compensated curve of the heart activity data that is defined by a heart rate and the post-exercise resting heart rate, and then the risk indicator is based upon the compensated curve during the prognostic period. Several specific aspects of this portion of the method 100 are described in more detail below.

In one embodiment, computation of the normalized heart rate recovery slope (stage 110) begins with the computation of the normalization factors that characterize the timing for the start of recovery and the post exercise resting heart rate. These factors are computed in stages 106 and 108.

Previous investigators have proposed an exponential curve known in the prior art of the general form:

$$HR=HR_{rest}+(HR_{peak}-HR_{rest}) \cdot e^{-kt} \quad (a)$$

to characterize the recovery process. In this equation, $HR_{rest}$ is the measured pre-exercise resting heart rate and $HR_{peak}$ is the peak exercise heart rate. The term $(HR_{peak}-HR_{rest})$ is defined as the pre-exercise heart rate reserve used in conventional techniques (i.e., the difference between the peak or maximum heart rate and the pre-exercise resting heart rate). An abnormal value for the pre-exercise heart rate reserve is well known to be prognostic for death. The decay coefficient k controls the rate of decay of the curve from peak heart rate through recovery, and t is the time measured from the beginning of recovery in minutes.

There are two important considerations that arise when fitting equation (a) to heart rate recovery data. First, the start of recovery is often difficult to pinpoint. Depending upon patient mobility and test protocol, there may be a transition period of 10-30 seconds when the patient is only in partial recovery as he/she moves from the exercise device to a supine position on an exam table. This time interval is a large fraction of the typical 1-2 minute post exercise interval commonly used to determine a metric of the heart rate reserve and can introduce errors into the metric. The second consideration is that post-exercise and pre-exercise resting heart rates are dynamic. It is fairly common to observe that the heart rate in recovery decays asymptotically over 5-10 minutes to a post-exercise resting heart rate distinctly different from the pre-exercise resting heart rate before the test. As shown in FIG. 3, for example, the difference between the pre- and post-exercise resting heart rates can be as large as 20-40 beats/min. As a result, the present inventor has discovered that forcing the heart rate recovery curve to return to a pre-exercise value for the resting heart rate can introduce systematic bias in the derived value of the decay coefficient k.

Figure 4:
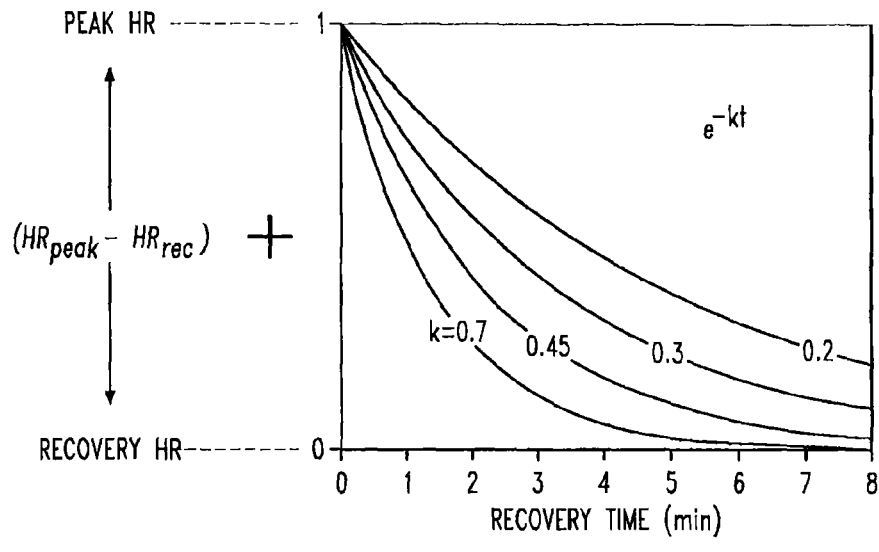
FIG. 4 illustrates the decomposition of the heart rate recovery curve into a scaling term and a normalized dynamic term that ranges from 1 at peak heart rate to 0 at the end of recovery.

One aspect of the method 100 (FIG. 1) is using a modified form to describe the heart rate recovery curve. The heart rate recovery curve can be decomposed into two elements: a normalized recovery curve that defines how quickly the peak heart rate ($HR_{peak}$) recovers to a stable recovery post-exercise resting rate ($HR_{rec}$), and an amplitude term defined by the difference between peak heart rate and the post-exercise resting heart rate ($HR_{peak}-HR_{rec}$). This decomposition provides a uniform comparison of heart rate recovery curve shapes for patients with significantly different heart rate reserves, and supports an assessment of the prognostic content of each element. A model in accordance with one embodiment of the invention that captures this decomposition is:

$$HR=HR_{rec}+(HR_{peak}-HR_{rec}) \cdot e^{-k(t-t_0)} \quad (b)$$

where the parameter k defines how quickly $e^{-kt}$ transitions from 1 to 0 as time t increases. FIG. 4 is a graphical representation of this decomposition which shows that the amplitude scaling is distinct from the rate of recovery defined by various values of k. The parameter $t_0$ represents the effective time delay between the protocol defined start of recovery (e.g., termination of exercise) and the physiological start. The parameters $HR_{rec}$, k and $t_0$ can be derived simultaneously through a least squares fit to the heart rate recovery data in one embodiment of the invention.

In several embodiments of the stages 108 and 110, computation of the normalized slope estimate for heart rate recovery involves fitting the functional form (b) to the decaying heart rate data. Although the curve can be fit using the instantaneous heart rate values, this would require more computational expense than necessary. For instance, in a 5 minute recovery period, there may be more than 500 beats which represent more than 500 simultaneous equations that must be solved to derive the three parameters. It is more efficient to create a limited series of estimates of heart rate, and associated measures of uncertainty, at discrete times during recovery and use this filtered data in the curve fitting process. The estimates may be derived from a series of time windows (e.g., [0-15 sec], [15-30 sec], and so on). In one example, stage 106 can include deriving a robust estimate of heart rate for each time range using a median average method where the individual R-R intervals are sorted shortest to longest in each window, and the middle half or other middle portion of the R-R intervals in each window are averaged to compute heart rates centered in time on the selected time intervals. This method reduces noise from the occasional R-R outliers. Once the median average heart rates for the time intervals have been computed, an estimate of the associated standard deviation is then computed.

Although there are many computational approaches to fitting curves, such as the curve defined by equation (b), to the heart rate data to derive $HR_{rec}$, k and $t_0$ for each patient test in stage 108, one particularly useful embodiment employs an iterative damped generalized inverse approach. For the equation (b), the partial derivatives of this equation can be analytically computed for $HR_{rec}$, k and $t_0$. Starting model estimates for $HR_{rec}$, k and $t_0$ can vary, but an example of starting parameters are:

HRrec=Post-test resting heart rate
k=~1.0 sec$^{-1}$
$t_0$=0 seconds.

Then, for each estimate of recovery heart rate at time t, the changes to these parameters that would lower the error in the fit between the model and the data are related by:

$$\frac{\partial HRR}{\partial HR_{rec}} \cdot \delta HR_{rec} + \frac{\partial HRR}{\partial k} \cdot \delta k + \frac{\partial HRR}{\partial t_0} \cdot \delta t_0 = \quad (c)$$

$$HRR_{Data}(t) - HRR_{Model}(t)$$

For the series of n estimates of heart rate, at increasing times $t_n$, this relationship may be written in matrix format as:

$$\begin{pmatrix} \frac{\partial HRR(t_1)}{\partial HR_{rec}} & \frac{\partial HRR(t_1)}{\partial HR_k} & \frac{\partial HRR(t_1)}{\partial HR_{t_0}} \\ \ldots & \ldots & \ldots \\ \frac{\partial HRR(t_n)}{\partial HR_{rec}} & \frac{\partial HRR(t_n)}{\partial HR_k} & \frac{\partial HRR(t_n)}{\partial HR_{t_0}} \end{pmatrix} \times \begin{pmatrix} \delta HR_{rec} \\ \delta HR_k \\ \delta HR_{t_0} \end{pmatrix} = \quad (d)$$

$$\begin{pmatrix} HRR_{Data}(t_1) - HRR_{Model}(t_1) \\ \ldots \\ HRR_{Data}(t_n) - HRR_{Model}(t_n) \end{pmatrix}$$

This may be written in a more convenient form as:

A×Model Changes=Error(between the data and the model), (e)

where A is the first matrix on the left of equation (d) which can be directly computed from equation (b). For a typical 5 minute recovery period, there would be about 20 estimates of heart rate at 20 distinct times representing 20 simultaneous equations to be solved to resolve the model changes that minimize the error. A stable solution to this matrix equation is:

Model Changes=$A^T(AA^T+(r/(1-r))V)^{-1}$(Error) (f)

Where: r damps the inverse:
=1: No Change
=0: Least Squares (often unstable)
V: Data Variance Setting the diagonal of the variance matrix to the individual estimates of the standard deviation of heart rate, for each time window, results in a weighting of the fit of the model based upon the uncertainty of each individual estimate of heart rate.

Figure 5:
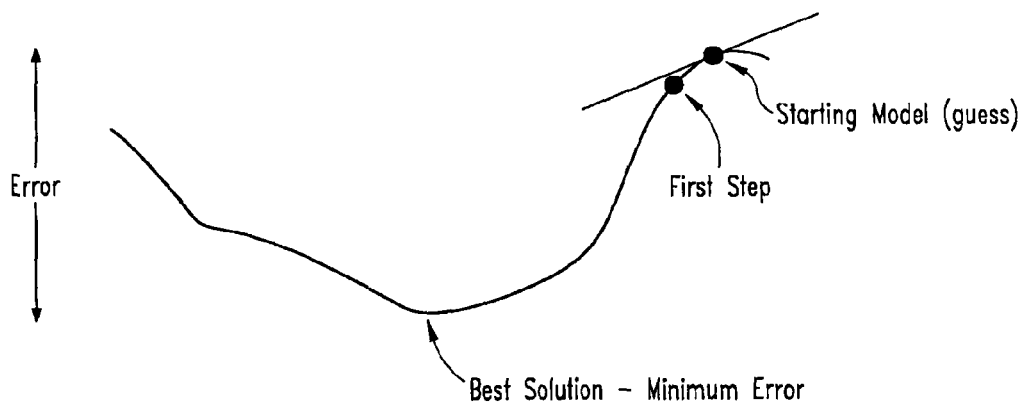
FIG. 5 illustrates the iterative solution methodology for fitting a heart rate recovery equation to the observed data for a patient.

FIG. 5 graphically illustrates how such an inversion proceeds. A starting guess is used to initially compute the derivatives and solve for the model changes that would lower the error. A small step is taken in this direction by updating the model parameters $HR_{rec}$, k and $t_0$ by a small percentage of the computed changes. The updated model is again used to re-compute the derivatives and equation (f) is again computed. The process continues until the model changes are acceptably small (e.g., 0.01 percent). The damping parameter r limits changes to the model parameters that are not well resolved by the data. Using this method, the inversion of heart rate recovery data is stable and low damping (r of approximately 0.1) is sufficient to achieve a rapid convergence to the minimum.

FIGS. 6A-6I show a suite of patient heart rate data from exercise testing of different patients and a heart rate curve fit to each. As shown in FIGS. 6A-6I, the curve fit is robust and very capable of capturing a wide range of decay curves, including cases with extreme heart rate variability and ectopy. For example, in a study of 1,959 patients the average standard deviation of the curves fit to the 15 second median averages from five or more minutes of recovery was less than 2.4 beats/min. As such, equation (b) accurately models the shape of the heart rate recovery curve and provides robust estimates for the start of recovery ($t_0$) and post-exercise heart rate reserve ($HR_{peak}-HR_{rec}$).

Once the parameter of the physiologic start of recovery $t_0$ and the post-exercise heart rate reserve ($HR_{peak}-HR_{rec}$) have been determined from the inverse approach in stage 108, the normalized heart rate curve estimates (e.g., compensated curves) can be computed from a consistent start of recovery by using the inverse of equation (b):

$HR_{norm}$=(HR-$HR_{rec}$)/($HR_{peak}$-$HR_{rec}$) (g)

Figure 7B:
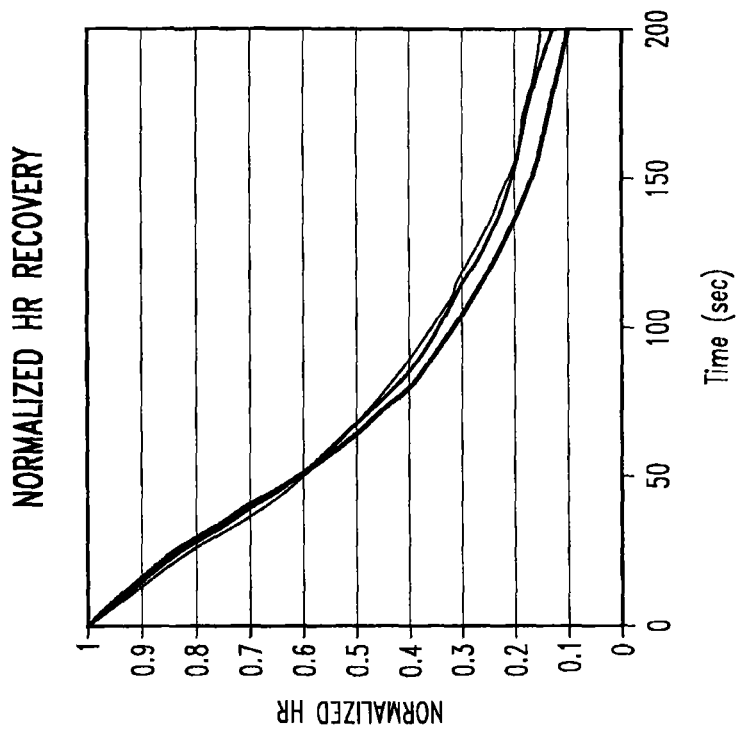
FIGS. 7A and 7B illustrate the normalization of the heart rate recovery curves to a common basis ranging from zero to one.
Figure 7A:
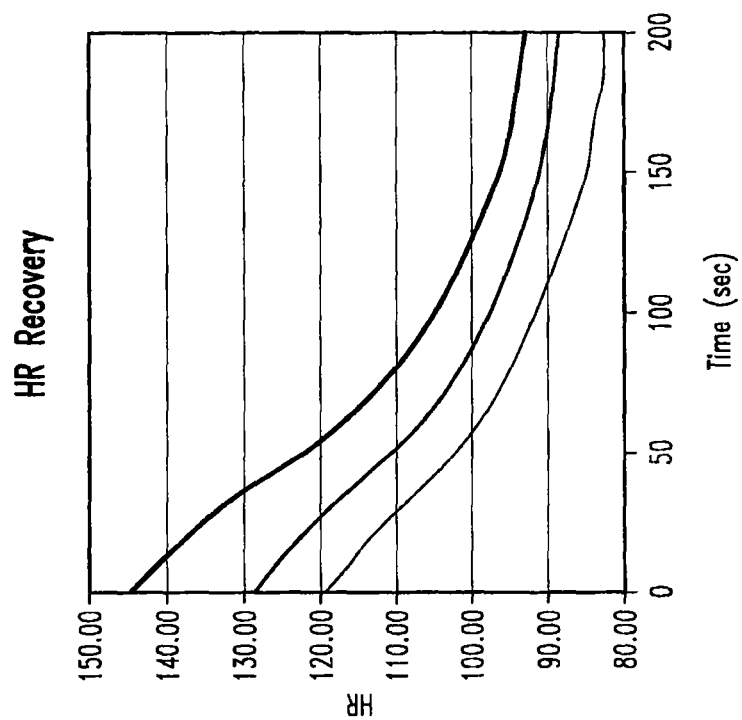

The step is illustrated in FIGS. 7A and 7B where the heart rate recovery curves for three patient populations have been normalized to a consistent range [0-1]. The divergence of the curves, and change in slopes, between the surviving and the dying cohorts at about 60 seconds in the normalized curves (FIG. 7B) is not graphically discernable in the raw recovery curves (FIG. 7A).

The normalized slop of the heart rate recovery curve can be computed in many ways and for different levels of resolution. As an example, a median average heart rate was computed for 15 second intervals from a consistent start of recovery time basis centered on 10 second increments through the first 200 second of recovery from heart rate data from 1,959 veterans (95% male, mean age 58±12 years) undergoing exercise treadmill testing. One form of normalized heart rate slope estimates (stage 110) for each 10 second interval were computed by differencing adjacent estimates of heart rate, and normalized by dividing by the scaling factor $(HR_{peak}-HR_{rec})$ derived by the inversion approach. This can then be multiplied by 100 for numerical convenience. For example:

$$HRRS_{15sec}=100\times(HR_{10sec}-HR_{20sec})/(HR_{peak}-HR_{rec}) \quad (h)$$

The heart rate recovery slope (HRRS) determined according to equation (h) is independent of heart rate reserve and believed to be sensitive to physiologic processes that may characterize subtle differences in heart rate behavior during recovery.

Figure 8:
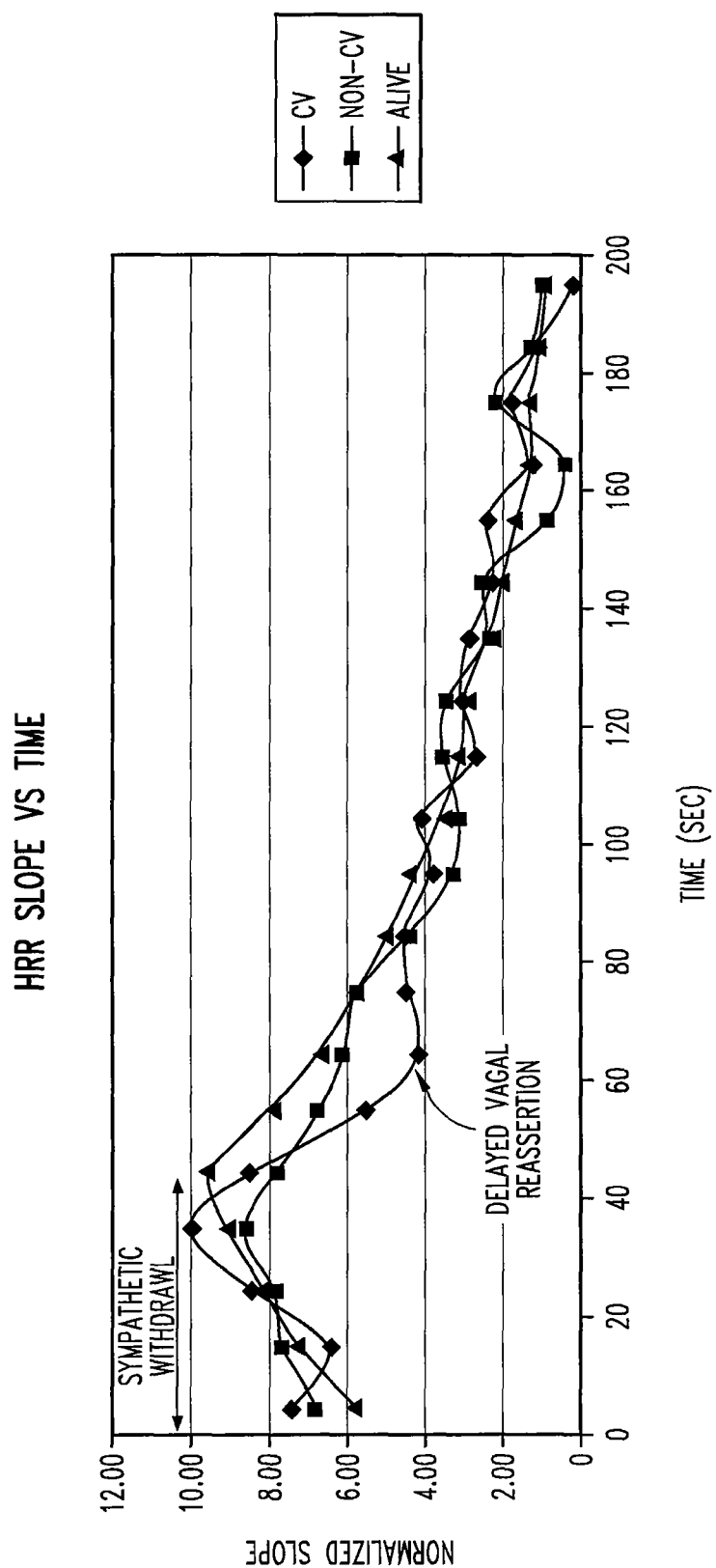
FIG. 8 illustrates a risk indicator, such as a normalized heart rate slope, over the first 200 seconds of recovery for three patient populations: (1) those dying of cardiovascular causes; (2) those dying of non-cardiovascular causes; and (3) survivors.

FIG. 8 shows heart rate recovery slopes ascertained in accordance with the invention over the first 200 seconds of recovery for a cohort dying of cardiovascular related causes (n=70), a cohort dying of non-cardiovascular related causes (n=117), and a surviving cohort (n=1,783) over the nearly five year average follow-up. As shown in FIG. 8, during the first 50 seconds of recovery the curves are nearly indistinguishable. The normalized slope estimates increase systematically (i.e.: the normalized slope of the heart rate decay rate increases) to a peak of about 9. For a heart rate reserve of 75 bpm, this would correspond to a decline rate of about 40 bpm. A difference in vagal response between any of the sub-populations of the studied cohort it is not apparent during the first 50 seconds of recovery. As such, this segment of the recovery for the sampled population set forth above is interpreted to primarily represent the accelerating increase in heart rate recovery as sympathetic stimulation is withdrawn, and this uniformly applies to the entire sampled population.

After 50 seconds into recovery, however, the curves diverge. The curve associated with patients with cardiovascular mortality shows a rapid decrease in the normalized heart rate recovery slope between 50 and 80 seconds. The decrease in the heart rate recovery slopes between 50 and 80 seconds is less in the cohort with non-cardiovascular mortality and much less in the surviving cohort. One potential interpretation of these results suggests that reassertion of vagal control of the heart rate in the surviving population drives rapid recovery of heart rate such that the heart rate recovery slope of this cohort remains relatively high during the prognostic period, while those that suffered cardiovascular mortality lacked the vagal tone necessary to continue the recovery initiated by sympathetic withdrawal such that the heart rate recovery slope of this cohort declined much more rapidly and remains relatively low during the prognostic period. In this embodiment, the difference in the reassertion of vagal down-regulation of heart rate as determined according to the normalized heart rate recovery slope between healthy patients and those suffering cardiovascular mortality is most statistically significant in the period 50-70 seconds into recovery for the 95% male population with an average age of 58±12 years.

Additional metrics can be used to characterize the normalized slope over the recovery interval. For example, a weighted least squares line was fit to the median average heart rate values using the normalized 10 second estimates and the associated standard deviations as discussed above and shown in equation (h). In another example, a second estimate was computed by fitting a least squares line to the normalized heart rate recovery values associated with every R-R interval over the prognostic period (e.g., the 50-70 second window $HRRS_{50-70}$) using equation (g). The first method provides equal weight to the average values in each ten second window. The second method tends to be weighted more strongly towards the earlier portion of the time window as there are more beat intervals associated with the higher heart rate. Those skilled in the art will recognize there are several similar methods for estimating the normalized slope of the heart rate recovery curve over a time window of interest. The exact time window for analysis may also be a function of patient age and sex. The example shown in FIG. 8 is for a predominately male cohort (95% male) with an average age of 58±12 years. The nature of the exercise protocol may also change the relevant time window because a recovery period with the patient in a supine position will have different characteristics that for patients that recover using a slow cool-down walk.

D. Assessing Risk—Stage 112

In one embodiment, the stage 112 provides an assessment of cardiac risk using a risk indicator based on the normalized slope of the heart rate recovery curve during the defined prognostic period. The risk indicator, for example, can be used in an age adjusted stepwise Cox multivariate model including the prognostic period, such as the 50-70 second normalized heart rate recovery slope ($HRRS_{50-70}$) and the heart rate variables of the post-exercise resting heart rate, the peak heart rate, the heart rate reserve, and the 1 and 2 minute heart rate recovery. In this example, only $HRRS_{50-70}$ and heart rate reserves were independent and significant predictors of cardiovascular relates morality, which confirms both the significant value of the heart rate recovery slope metric as a risk indicator and the expected decoupling from heart rate reserve. Subjects in the lowest quartile for the heart rate recovery slope metric had an adjusted relative risk of cardiovascular related mortality of 1.7 (95% Cl 1.2-2.4, p=0.002) when compared to all other subjects.

Figure 9:
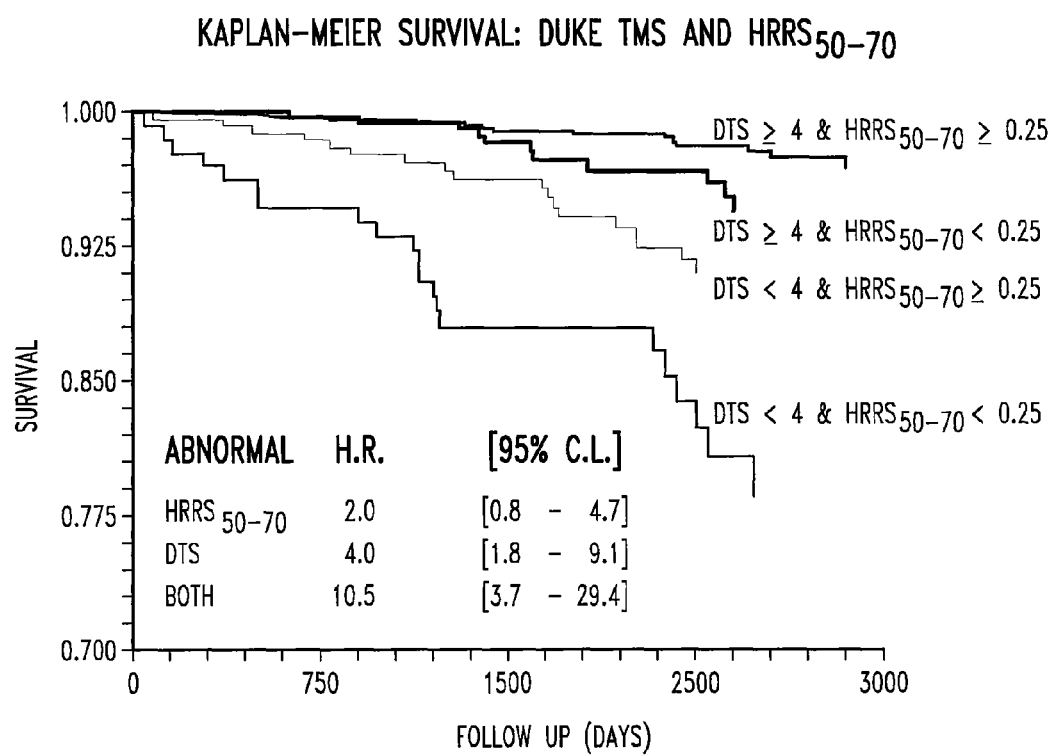
FIG. 9 illustrates a Kaplan-Meier assessment of survival for patients with abnormal values for the Duke Treadmill Score and for a heart rate recovery slope metric in accordance with the invention.

Risk assessment methodologies using Cox proportional hazard and Kaplan-Meier survival analysis are well known to those familiar with statistical analysis in the medical industry. The heart rate recovery slope risk indicator has been assessed relative to the existing Duke Treadmill Score (TMS), the current industry "gold" standard exercise based prognostic metric for risk stratification. FIG. 9 shows the survival analysis for the four combinations of normal and abnormal measures for the Duke TMS and HRRS metric. An abnormal HRRS metric increases a patient's risk of cardiovascular death by 2.0 [95% CL: 0.8-4.7] times over a normal score. An abnormal Duke TMS score increases a patients risk to 4.0 [95% CL: 1.8-9.1] times greater than normal. A Cox proportional hazard analysis shows that the Duke TMS metric is an independent parameter, distinct from HRV Slope, and the combined Kaplan-Meier hazard ratio when both metrics are abnormal is 10.5 [95% CL: 3.7-29.4] times greater, a significant increase in risk over the estimate based upon the current gold standard Duke TMS. The new heart rate recovery slope metric appears to quantify vagal tone, is complimentary to the Duke TMS, and provides a significant improvement in risk assessment when used together.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A method for assessing cardiac risks based on heart activity data obtained during a recovery stage of an exercise test of a specific patient, comprising:
    determining a prognostic period of the heart activity data after a time t0 after a peak heart rate of the exercise test;
    ascertaining a risk indicator based on (a) the heart activity data during the recovery stage only after time t0 and (b) a post-exercise heart rate reserve based on a post-exercise resting heart rate; and
    providing an assessment of cardiac risk of the specific patient based on the ascertained risk indicator wherein the time t0 is an effective time delay between a protocol defined start of the recovery stage and a subsequent physiological start of the recovery stage after termination of exercise.

2. The method of claim 1 wherein the method further comprises:
determining the time t0 and the post-exercise resting heart rate by (a) measuring the peak heart rate (HRpeak) at a time t at which the patient terminates exercising and (b) fitting the time t0 and the post-exercise resting heart rate to the heart activity data during the recovery stage;
determining a compensated curve of the heart activity data defined by a heart rate and the post-exercise resting heart rate; and
determining a risk indicator based upon the compensated curve during the prognostic period.

3. The method of claim 2 wherein fitting the time t0 and the post-exercise resting heart rate to the heart activity data during the recovery stage comprises iteratively fitting the post-exercise resting heart rate (HR rec), a decay coefficient (k), and the time t0 to the heart rate activity data according to a curve defined by:

$$HR=HRrec+(HRpeak-HRrec)e-k(t-t0)$$

4. The method of claim 3 wherein the post-exercise heart rate reserve is defined by (HRpeak−HRrec).

5. The method of claim 2 wherein fitting the time t0 and the post-exercise resting heart rate to the heart activity data during the recovery stage comprises iteratively fitting the post-exercise resting heart rate (HRrec), a decay coefficient (k), and the time t0 to the heart rate activity data according to an iterative damped generalized inverse approach using partial derivatives of a post-exercise resting heart rate, k and t0.

6. The method of claim 2 further comprises generating a curve of the heart activity data by (a) defining time windows of the heart activity data, (b) sorting heart rates within the time windows, and (c) averaging at least a portion of the heart rates in each window centered on a median heart rate in each window.

7. The methods of claim 2 further comprising generating a compensated curve by subtracting the post-exercise resting heart rate from the heart activity data to provide a differenced result and dividing the differenced result by the post-exercise heart rate reserve.

8. The method of claim 2 wherein:
ascertaining the risk indicator comprises determining a slope of the compensated curve during the prognostic period; and
providing an assessment of cardiac risk comprises comparing the risk indicators for a cohort having experienced a cardiac event with the risk indicator of the patient.

9. A method for assessing cardiac risks based on heart activity data obtained during a recovery stage of an exercise test of a specific patient, comprising:
determining a post-exercise resting heart rate and prognostic period after a time t0 after a peak heart rate, wherein the time t0 is an effective time delay between a protocol defined start of the recovery stage and a subsequent physiological start of the recovery stage after terminating exercise;
determining a slope of a post-exercise heart rate recovery after time t0 based on the post-exercise resting heart rate; and
providing a cardiac risk assessment of the patient based on the determined slope of the post-exercise heart rate recovery.

10. The method of claim wherein determining the time t0 and the post-exercise resting heart rate comprises (a) measuring the peak heart rate (HRpeak) at a time t at which the patient terminates exercise and (b) fitting the time t0 and the post-exercise resting heart rate to the heart activity data during the recovery stage, and the method further comprises determining a compensated curve of the heart rate activity defined by a heart rate during the prognostic period and the post-exercise resting heart rate.

11. The method of claim 10 wherein fitting the time t0 and the post-exercise resting heart rate to the heart activity data during the recovery stage comprises iteratively fitting the post-exercise resting heart rate (HRrec), a decay coefficient (k), and the time t0 to the heart rate activity data according to a curve defined by:

$$HR=HRrec+(HRpeak-HRrec)e-k(t-t0)$$

12. The method of claim 11 wherein the post-exercise heart rate reserve is defined by (HRpeak-HRrec).

13. The method of claim 10 wherein fitting the time t0 and the post-exercise resting heart rate to the heart activity data during the recovery stage comprises iteratively fitting the post-exercise resting heart rate (HRrec) a decay coefficient (k), and the time t0 to the heart rate activity data according to an iterative damped generalized inverse approach using partial derivatives of the post-exercise resting heart rate, k and t0.

14. The method of claim 12 further comprising:
ascertaining a heart rate recovery value comprising determining a slope of the compensated curve wherein the compensated curve is generated by subtracting the post-exercise resting heart rate from the heart rate during the prognostic period to provide a differenced result and dividing the differenced result by the post-exercise heart rate reserve.

15. A method for assessing cardiac risks based on heart activity data obtained during a recovery stage of an exercise test of a specific patient, comprising:
providing heart rate recovery slopes of a sample of a cohort that has experienced a cardiac event (HRRScv);
providing heart rate recovery slopes of a sample of the cohort that has not experienced a cardiac event (HRRSlive);
selecting a prognostic period of the recovery stage for the specific patient where HRRSlive is statistically separate from HRRScv;
determining a heart rate recovery slope of the patient during the prognostic period; and
ascertaining a cardiac risk for the patient based on the heart rate recovery slope of the patient, HRRSlive, and HRRScv wherein providing a prognostic period comprises selecting a prognostic period start time after a time t0 wherein the time t0 is an effective time delay between a protocol defined start of the recovery stage and a subsequent physiological start of the recovery stage after termination of exercise.

16. A method for assessing cardiac risks based on heart activity data obtained during a recovery stage of an exercise test of a specific patient, comprising: providing a prognostic period during the recovery stage after sympathetic control of a heart is subordinate to vagal control of the heart; and ascertaining a cardiac risk for the patient based on a slope of the heart activity data during only the prognostic period wherein providing a prognostic period comprises selecting a prognostic period start time after a time t0 wherein the time t0 is an effective time delay between a protocol defined start of the recovery stage and the subsequent physiological start of the recovery stage after termination of exercise.

17. A system for assessing cardiac risks based on heart activity data obtained during a recovery stage of an exercise test of a specific patient, comprising:
- a cardiographic device configured to measure the heart activity data; and
- a computer having a computer-operable medium containing instructions that—
  - (a) determines a prognostic period of the heart activity data after a time t0 after a peak heart rate of the exercise test;
  - (b) ascertains a risk indicator based on (a) the heart rate activity data during the recovery stage only after time t0 and (b) a post-exercise heart rate reserve value based on a post-exercise resting heart rate; and
  - (c) provides an assessment of cardiac risk of the specific patient based on the ascertained risk indicator
- wherein the time t0 is an effective time delay between a protocol defined start of the recovery stage and a subsequent physiological start of the recovery stage after termination of exercise.

18. The system of claim 17 wherein the instructions of the computer-operable medium further:
- determines the time t0 and the post-exercise resting heart rate by (a) measuring the peak heart rate (HRpeak) at a time at which the patient terminates exercising and (b) fitting the time t0 and the post-exercise resting heart rate to the heart activity data during the recovery stage; and
- determines a compensated curve of the heart rate activity defined by a heart rate during the prognostic period and the post-exercise resting heart rate.

19. The system of claim 18 wherein instructions of the computer-operable medium further:
- ascertain the risk indicator by determining a slope of the compensated curve; and
- provide an assessment of cardiac risk by comparing a slope of a corresponding compensated curve for a cohort that has experienced a cardiac event and the slope of the compensated curve of the patient.

20. A system for assessing cardiac risks based on heart activity data obtained during a recovery stage of an exercise test of a specific patient, comprising:
- a cardiographic device configured to measure the heart activity data; and
- a computer having a computer-operable medium containing instructions that—
  - (a) determines a post-exercise resting heart rate and a start of a prognostic period after a time t0 after a peak heart rate, wherein the time t0 is an effective time delay between a protocol defined start of the recovery stage and a subsequent physiological start of the recovery stage after termination of exercise;
  - (b) determines a slope of a post-exercise heart rate recovery after time t0 based on the post-exercise resting heart rate; and
  - (c) provides a cardiac risk assessment of the patient based on the determined slope of the post-exercise heart rate recovery.

* * * * *

UNITED STATES PATENT AND TRADEMARK OFFICE
CERTIFICATE OF CORRECTION

| | | |
|---|---|---|
| PATENT NO. | : 9,149,195 B2 | Page 1 of 1 |
| APPLICATION NO. | : 11/733699 | |
| DATED | : October 6, 2015 | |
| INVENTOR(S) | : David M. Hadley | |

It is certified that error appears in the above-identified patent and that said Letters Patent is hereby corrected as shown below:

In the claims,

Column 11, line 66 the portion reading "10. The method of claim wherein determining the time t0" should read --10. The method of claim 9 wherein determining the time t0--.

Signed and Sealed this
Sixteenth Day of February, 2016

Michelle K. Lee
*Director of the United States Patent and Trademark Office*